United States Patent [19]

Schuster et al.

[11] Patent Number: 5,616,817
[45] Date of Patent: Apr. 1, 1997

[54] PREPARATION OF 1,2-PROPANEDIOL

[75] Inventors: Ludwig Schuster, Limburgerhof; Manfred Eggersdorfer, Frankenthal, both of Germany

[73] Assignee: BASF Aktiengesellschaft, Ludwigshafen, Germany

[21] Appl. No.: 559,625

[22] Filed: Nov. 20, 1995

[30] Foreign Application Priority Data

Nov. 26, 1994 [DE] Germany ............ 44 42 124.9

[51] Int. Cl.⁶ ............ C07C 29/132; C07C 29/60; C07C 31/20
[52] U.S. Cl. ............................................ 568/861
[58] Field of Search ................................. 568/861

[56] References Cited

U.S. PATENT DOCUMENTS

| 5,107,018 | 4/1992 | Schuster . |
| 5,210,335 | 5/1993 | Schuster et al. ............ 568/861 |
| 5,306,847 | 4/1994 | Gehrer et al. ............ 568/861 |

FOREIGN PATENT DOCUMENTS

| 382050 | 8/1990 | European Pat. Off. . |
| 415202 | 3/1991 | European Pat. Off. . |
| 523014 | 1/1993 | European Pat. Off. . |
| 523015 | 1/1993 | European Pat. Off. . |
| 2321101 | 4/1973 | Germany . |
| 4302464 | 8/1994 | Germany . |
| 108184 | 8/1958 | Pakistan ............ 568/861 |
| 91/11845 | 8/1991 | WIPO . |

OTHER PUBLICATIONS

BASF patent specification OZ 0050/40557 (equivalent to European 382 050).

*Primary Examiner*—Joseph E. Evans
*Attorney, Agent, or Firm*—Keil & Weinkauf

[57] ABSTRACT

A process for the preparation of 1,2-propanediol by catalytic hydrogenation of glycerol at elevated temperature and elevated pressure, which comprises using glycerol having a water content of up to 20% by weight and a catalyst comprising the metals cobalt, copper, manganese and molybdenum in amounts of, based on the total weight of the catalyst, from 40 to 70% by weight of cobalt,
from 10 to 20% by weight of copper,
from 0 to 10% by weight of manganese and
from 0 to 10% by weight of molybdenum, where this catalytically active material may additionally contain inorganic polyacids and/or heteropolyacids in an amount of up to 10% by weight, based on the total weight of the catalyst.

1 Claim, No Drawings

PREPARATION OF 1,2-PROPANEDIOL

The present invention relates to a process for the preparation of 1,2-propanediol by catalytic hydrogenation of glycerol at elevated temperature and pressure, which comprises using glycerol having a water content of up to 20% by weight and a catalyst comprising the metals cobalt, copper, manganese and molybdenum in amounts of, based on the total weight of the catalyst, from 40 to 70% by weight of cobalt, from 10 to 20% by weight of copper, from 0 to 10% by weight of manganese and from 0 to 10% by weight of molybdenum, where this catalytically active material may addtionally contain inorganic polyacids and/or heteropolyacids in an amount of up to 10% by weight, Based on the total weight of the catalyst.

The hydrogenation of glycerol to 1,2-propanediol has already been investigated a number of times, but the unsatisfactory selectivity has prevented use in industrial production. Two recent patent applications describe the hydrogenation of glycerol on modified ruthenium supported catalysts (EP-A--0 523 014) and on zinc/copper catalysts (EP-A-0 523 015). Even though certain advances over the earlier work have been achieved therein, these procedures still have some disadvantages.

For example, both applications carry out the hydrogenolysis reaction in very dilute aqueous solutions. The 30% solutions of glycerol in water which are used predominantly become further diluted through the water of reaction that is formed. In order to isolate propanediol, it is therefore necessary first to remove a large amount of water by distillation, which means expenditure of a large amount of energy.

Furthermore, the selectivity is still unsatisfactory. Virtually quantitative conversion is achieved at the expense of selectivity. For batch processes, selectivities of only from 75 to 84% are then generally achieved.

In order to achieve 100% conversion, from 10 to 45% by weight of sodium hydroxide, based on glycerol, was additionally necessary in the case of the ruthenium catalyst in EP-A-0 523 014. EP-A-0 415 202 describes a process for the preparation of lower polyhydric alcohols by catalytic hydrogenation of aqueous sucrose solutions at elevated temperature and pressure using a catalyst whose active material essentially comprises the metals cobalt, copper and manganese.

It is an object of the present invention to provide a process for the preparation of 1,2-propanediol by catalytic hydrogenation of glycerol at elevated temperature and elevated pressure which does not have the disadvantages outlined above.

We have found that this object is achieved by the process defined at the outset.

The catalyst employed in the novel process generally contains essentially no catalyst supports and, in addition to cobalt and copper, preferably comprises manganese and molybdenum, phosphoric acid and phosphate.

In a preferred embodiment, the catalyst comprises from 40 to 70% by weight of cobalt (as CoO), from 13 to 17% by weight of copper (as CuO) and from 3 to 8% by weight of manganese (as $MnO_2$), and from 0.1 to 5% by weight of phosphorus (as $H_3PO_4$) and from 0.5 to 5% by weight of molybdenum (as $MoO_3$), in each case based on the total weight of the catalyst.

Particular preference is given to catalysts comprising from 55 to 70% by weight of CoO, from 13 to 17% by weight of CuO, from 4 to 6% by weight of $MnO_2$, from 1 to 3% by weight of phosphorus (as phosphoric acid) and from 1 to 4% by weight of $MoO_3$.

The catalysts used in the novel process are generally prepared by co-precipitating these metals, for example as oxides, hydroxides, oxide hydrates, basic salts or carbonates, from a solution of their salts, for example their nitrates or acetates, by addition of a base, advantageously an aqueous mineral base such as sodium hydroxide solution, potassium hydroxide solution or sodium carbonate solution, and separating off, drying and calcining the precipitate. The precipitation is preferably carried out by the process described in DE-A-23 21 101.

Before use in the novel process, the catalyst obtained in this way is activated by reduction using hydrogen, during which all or some of the metal compounds present therein are reduced to the corresponding metals. In general, this reduction is carried out at elevated temperature, preferably at from 200° to 400° C., in a stream of hydrogen.

Catalysts having particularly advantageous mechanical properties can be obtained by mixing the metal salt solution, before the precipitation, with inorganic acids which are capable of forming polyacids or heteropolyacids, such as sulfuric acid, boric acid, phosphoric acid, molybdic acid, vanadic acid or tungstic acid, or salts thereof, such as trisodium phosphate, sodium tetraborate, potassium dihydrogenphosphate, calcium hydrogenphosphate, magnesium hydrogenborate, aluminum phosphate, sodium molybdate, ammonium molybdate, ammonium vanadat and/or sodium tungstate, and then carrying out the precipitation and further treatment of the precipitate as described in EP-A-0 415 202.

The composition of the hydrogenation products obtainable using the catalysts described depends on the reaction temperature selected. For example, particularly high yields of 1,2-propanediol are achieved if the novel hydrogenation of glycerol is carried out at from 180° to 270° C., preferably at from 200° to 250° C.

The hydrogenation of glycerol is generally carried out, in accordance with the invention, using hydrogen pressures of from 100 to 700 bar, preferably at pressures of from 200 to 325 bar. At lower pressures the reaction is too slow and incomplete, while at pressures above 700 bar monohydric alcohols are increasingly formed. It is even possible for increasing chain cleavage to occur.

In the novel process, preference is given to the hydrogenation of glycerol of very high concentration, for example from the monohydrate to pure glycerol. The hydrogenation of low-concentration glycerol solutions having a water content of up to 20% by weight is likewise potentially successful regarding the composition of the hydrogenation product, but is inefficient owing to the reduced space-time yield. This also applies to the concentration of the aqueous solutions, which requires more energy.

It is also possible in accordance with the invention to employ nonaqueous solutions, for example in methanol, but this has no significant advantage over concentrated glycerol.

Glycerol obtained from the transesterification of fats and oils should expediently be freed from catalyst poisons, such as sulfur, before hydrogenation in the novel process. This is achieved, for example, by simple short-path distillation. In the case of crude glycerol containing the sulfuric acid which is frequently used as transesterification catalyst, simple treatment with ion exchangers may be sufficient.

The invention has numerous advantages. For example, highly concentrated glycerol, for example the monohydrate containing 86% by weight of glycerol, or even pure glycerol, can be selectively hydrogenated to 1,2-propanediol in yields of, generally, up to 95%.

In addition, the novel hydrogenation gives selectivities of up to 95% with 100% conversion both in autoclaves and in trickle reactors filled with granular catalyst. A small amount of methanol, ethanol, isopropanol and 1,3-propanediol is also formed.

The percentages in the examples are by weight.

EXAMPLES

Example 1

700 g of 99.5% purity glycerol and 50 g of a catalyst comprising 68% by weight of cobalt (as CoO), 17% by weight of copper (as CuO) and 6% by weight of manganese (as $MnO_2$) and 4% by weight of phosphorus (as $H_3PO_4$) and 5% by weight of molybdenum (as $MoO_3$) were introduced into a 1.2 l autoclave fitted with a high-speed gas-dispersion stirrer. The catalyst had previously been reduced at 300° C. using hydrogen.

In the cold state, hydrogen was then injected to a pressure of 50 bar, and the autoclave was then heated to 250° C. When this reaction temperature had been reached, the pressure was raised to 250 bar and kept at this level by re-injection. After 6 hours, the autoclave was cooled and emptied and the catalyst was filtered off from the contents. 687 g of reaction mixture having a water content of 23.6% were obtained.

Analysis by HPLC using an Aminex HPX 87C column and a refractive index detector showed that the reaction mixture contained 95.8% by weight of 1,2-propanediol and 3.2% by weight of n-propanol. No glycerol was detected.

Example 2

The reactor used for the continuous version of the novel process was a trickle tower with a length of 10 m and an internal diameter of 4.5 cm. The hydrogenation column was filled with 21.9 kg of the catalyst described under Example 1. The catalyst was converted into the metallic state by slow heating to 300° C., first in an $H_2/N_2$ mixture containing 10% of hydrogen, then rising to pure hydrogen.

The reaction conditions were as follows:

Feed: 86.5% purity glycerol (remainder water)

Pressure: 295 bar

Temperature: 210° to 220° C.

Liquid circulation: 35 l/h=22 $m^3/m^2h$

Gas circulation: 0 to 2.5 $m^3/h$

Offgas: 2.5 m3/h

Feed: 1.5 kg/h

The water content of the resultant reaction mixture was from 29 to 30%.

Analysis of the organic constituents, again by HPLC with an Aminex column, showed 92% by weight of 1,2-propanediol and 4.3% by weight of n-propanol in addition to small amounts of lower alcohols, but no glycerol.

We claim:

1. A process for the preparation of 1,2-propanediol by catalytic hydrogenation of glycerol at elevated temperature and pressure, which comprises using glycerol having a water content of up to 20% by weight and a catalyst comprising the metals cobalt, copper, manganese and molybdenum in amounts of, based on the total weight of the catalyst, from 40 to 70% by weight of cobalt, from 10 to 20% by weight of copper, from 0 to 10% by weight of manganese and from 0 to 10% by weight of molybdenum, where this catalytically active material may additionally contain inorganic polyacids and/or heteropolyacids in an amount of up to 10% by weight, based on the total weight of the catalyst.

* * * * *